United States Patent
Vértesy et al.

(10) Patent No.: US 6,472,158 B1
(45) Date of Patent: Oct. 29, 2002

(54) USTILIPIDES, METHOD FOR THE PRODUCTION AND THE USE THEREOF

(75) Inventors: Laszló Vértesy, Eppstein; Michael Kurz, Hofheim; Gerhard Noelken, Sulzbach; Joachim Wink, Rödermark, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/600,759

(22) PCT Filed: Jan. 19, 1999

(86) PCT No.: PCT/EP99/00288
§ 371 (c)(1),
(2), (4) Date: Jul. 21, 2000

(87) PCT Pub. No.: WO99/37658
PCT Pub. Date: Jul. 29, 1999

(30) Foreign Application Priority Data

Jan. 23, 1998 (DE) .......................................... 198 02 450

(51) Int. Cl.⁷ .................... C07H 15/14; C12P 19/02; A61R 31/71; G01N 33/53
(52) U.S. Cl. .......................... 435/7.1; 514/183; 435/6; 435/254.1
(58) Field of Search ................................ 435/7.1, 91.4, 435/6, 91.1, 254.1; 536/500; 514/2, 183

(56) References Cited

U.S. PATENT DOCUMENTS 4,582,823 A    4/1986   Heffner et al. ................. 514/46
6,297,217 B1 * 10/2001  Adams et al. ................. 514/18

OTHER PUBLICATIONS

Obermeier, A;Bradshaw, R.; Seedorf, E.; Choides, A.; Schlessinger, J.; Ullrich,A.; "Neruonal Differentiation Signals are Controlled By Nerve Growth Factor Receptor/Trk Bing=ding sites for SHC and PLC.gamma" EMBO. J. (1994), 13V(7), 1585–90.*

Kobayashi, M. et al "Penaresin, A New Sarcoplasmic Reticulul Ca–Inducer from the Okinawan Marine Sponge Penares SP." Heterocycles, 1990, vol. 31, 2205–2218.*

Guiavita, N. k., "Eryloside From An Alantic Sponge Erylus goffrilleri", Tetrahedron Letters., vol. 35 No. 25 4299–4302.*

Kobayashi, M. et al "Marine Natural Products. XXVIII. The Structure of Sarasinosides, Nine Norlanostane–Triterpenoidal Oligoglycosides from the Palauan Marine Sponge Asteropus Sarasinosum," Chem. Pharm. Bull., 1991, 39(11), 2867–2877.*

Kobayashi, M. et al "Penaresidin A and B, Two Novel Azetidine Alkaloids with Potent Actomysin ATPase–Activating Activity form the Owkinawan Marine Sponge Penares sp." J. Chem. Soc. Perkin Trans., 1991, (1), 1135–1137.*

Carmely et al., "The Structure of Eryloside A, A New Antitumor and Antifungal 4–Methylated Steroidal Gylcoside from the Sponge Erylus Lendenfeldi" J. Nat. Prod., vol. 52, No. 1, 1989 167–170.*

Takei, M. et al., "Mechanism of Inhibition of IgE–Dependent Histamine Release from Rat Mast Cells by Penasterol and Penasterone," J. Pharm. Sci., vol. 84, No 2, 1995.*

Soriente et al., "Enzymatic Regio–and Diastereoselective Hydrolysis of Peracetylated Glycerol–and Erythritol–B–Glucosides," Bioorganic & Medicinal Chemistry Letters, vol. 5, pp. 2321–2324 (1995).

Deml et al., "Schizonellin A and B, New Glycolipids from Schizonella Melanogramma," Phytochemistry, vol. 19, pp. 83–87 (1980).

Kaneda et al., "Liliosides D and E, Two Glycerol Glucosides from Lilium Japonicum," Phytochemistry, vol. 23, pp. 795–798 (1984).

Sokoloff et al., "Molecular cloning and characterization of a novel dopamine receptor ($D_3$) as a target for neuroleptics," Nature, vol. 347, pp. 146–151 (1990).

Kreiss et al., "Dopamine receptor agonist potencies for inhibition of cell firing correlate with dopamine $D_3$ receptor binding affinities," Eur. J. Pharmacol. vol. 277, pp. 209–214 (1995).

* cited by examiner

Primary Examiner—Kenneth R. Horlick
Assistant Examiner—Christine Maupin
(74) Attorney, Agent, or Firm—Finnegan, Henderson, Farabow, Garrett & Dunner, LLP

(57) ABSTRACT

New active agents (ustilipides) formed by the microorganism Ustilago maydis, FH 2634, DSM 11494 during fermentation. The invention also relates to a method for the production of said ustilipides and to their use as medicaments in the treatment of schizophrenia or diseases caused by dopamine metabolic dysfunction. The invention further relates to medicaments containing ustilipides and to the microorganism Ustilago maydis, FH 2634, DSM 11494.

26 Claims, No Drawings

USTILIPIDES, METHOD FOR THE PRODUCTION AND THE USE THEREOF

This application is a national stage filing under 35 U.S.C. § 371 of international application No. PCT/EP99/00288, filed on Jan. 19,1999.

The present invention relates to novel active substances (ustilipides) which are formed by the microorganism Ustilago maydis, FH 2634, DSM 11494, during fermentation, to a method for the production thereof, to the use thereof as pharmaceutical, to ustilipide-containing pharmaceuticals and to the microorganism Ustilago maydis, FH 2634, DSM 11494.

Schizophrenia (dementia praecox) is an endogenous, psychosomatic disorder with loss of the structural cohesion of the personality and with disconnection of thought, affect and perception. It is based on the interaction of psychological and somatic factors. Schizophrenia is associated with severe disorders of thought, disturbances of drive, delusions, hallucinations and disturbances of the perception of self. Treatment of schizophrenia at present is mainly by the administration of neuroleptics, and by psychotherapy. It can at present not yet be cured, or can be cured to only a limited extent. Because the possibility of treating this severe disorder is completely inadequate, there is an urgent need for novel medicines suitable for treating schizophrenia.

It has now been found that the strain Ustilago maydis, FH 2634, DSM 11494, is able to form novel, highly active substances which are suitable for treating schizophrenia or other diseases caused by dysfunction of dopamine metabolism, and which are also well tolerated.

The invention accordingly relates to the active substances (ustilipides) formed by the strain Ustilago maydis DSM 11494, and to their physiologically tolerated salts, esters and obvious chemical equivalents.

The invention thus relates to compounds of the formula I

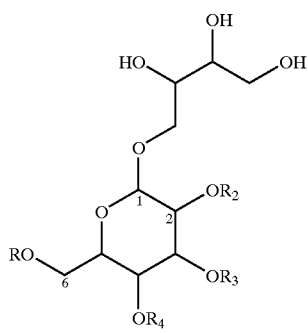

(I)

where $R_2$, $R_3$ and $R_4$ are, independently of one another, acyl radicals with 2–25 carbon atoms, preferably with 2–20 carbon atoms, which are unsubstituted or are substituted, independently of one another, by 1, 2 or 3 ($C_6$–$C_{12}$)-aryl radicals; and R is hydrogen or a radical defined under $R^2$, $R^3$ and $R^4$ where in the case where R is hydrogen, then $R^2$ is an acyl radical with 3–25 carbon atoms, preferably with 3–20 carbon atoms, which is unsubstituted or substituted by 1, 2 or 3 ($C_6$–$C_{12}$)-aryl radicals;

and the physiologically tolerated salts thereof.

Preference is given to compounds of the formula I in which

R is hydrogen or an acyl radical with 2–25 carbon atoms, preferably with 2–20 carbon atoms;

$R^2$ is an acyl radical with 4–25 carbon atoms, preferably with 4–20 carbon atoms;

$R^3$ is an acyl radical with 10–25 carbon atoms, preferably with 15–20 carbon atoms; and $R^4$ is an acyl radical with 2–25 carbon atoms, preferably with 2–20 carbon atoms;

and the physiologically tolerated salts thereof.

Preference is also given to compounds of the formula I in which $R^3$ is an acyl radical with 10–20 carbon atoms, preferably 15–18 carbon atoms, and R, $R^1$, $R^3$ and $R^4$ are each, independently of one another, an acyl radical with 2–10 carbon atoms, particularly preferably with 2–6 carbon atoms, and the physiologically tolerated salts thereof.

The acyl radicals in the compounds of the formula I can be straight-chain or branched, saturated or unsaturated once, twice, three times, four times or five times.

An acyl radical with 2 carbon atoms means, for example, an acetyl radical.

Examples of saturated, unbranched acyl radicals are an acetic acid residue (C=2), propionic acid residue (C=3), butyric acid residue (C=4), valeric acid residue (C=5), caproic acid residue (C=6), enanthic acid residue (C=7), caprylic acid residue (C=8), pelargonic acid residue (C=9), capric acid residue (C=10), undecanoic acid residue (C=11), lauric acid residue (C=12), tridecanoic acid residue (C=13), myristic acid residue (C=14), pentadecanoic acid residue (C=15), palmitic acid residue (C=16), margaric acid residue (C=17), stearic acid residue (C=18), nonadecanoic acid residue (C=19), arachidic acid residue (C=20), behenic acid residue (C=22), lignoceric acid residue (C=24). Examples of saturated, branched acyl radicals are an isobutyric acid residue (C=4), isovaleric acid residue (C=5), tuberculostearic acid residue (C=19).

Examples of unbranched acyl radicals which are unsaturated once are an acrylic acid residue (C=3), crotonic acid residue (C=4), palmitoleic acid residue (C=16), oleic acid residue (C=18), erucic acid residue (C=22).

Examples of unbranched acyl radicals which are unsaturated twice are a sorbic acid residue (C=6) and linoleic acid residue (C=18).

Examples of unbranched acyl radicals which are unsaturated three times are a linolenic acid residue (C=18) or eleostearic acid residue (C=18).

An example of an unbranched acyl radical which is unsaturated four times is an arachidonic acid residue (C=20).

An example of an unbranched acyl radical which is unsaturated five times is a clupanodonic acid residue (C=22). ($C_6$–$C_{12}$)-aryl means, for example, phenyl, naphthyl or biphenylyl. Phenyl is preferred.

The invention further relates to
a) a compound of the formula (II)

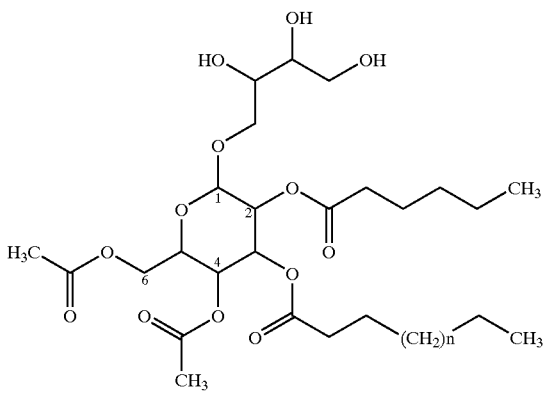

(II)

where n is 11 (=ustilipide A: molecular formula: $C_{36}H_{64}O_{13}$, MW: 704) and the physiologically tolerated salts thereof;
b) a compound of the formula (III)

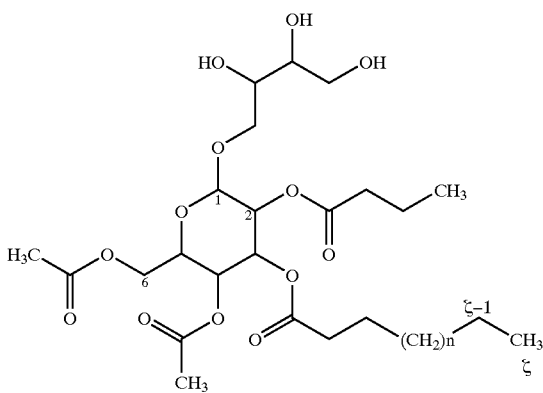

(III)

where n is 11 (=ustilipide B: molecular formula: $C_{34}H_{60}O_{13}$, MW: 676) and the physiologically tolerated salts thereof; and
c) a compound of the formula (IV)

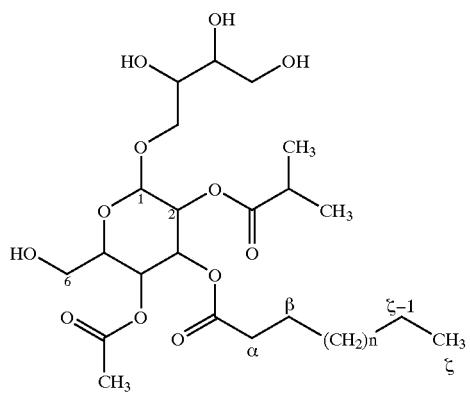

(IV)

wherein n is 11 (ustilipide C, molecular formula: $C_{32}H_{58}O_{12}$, MW: 634) and the physiologically tolerated salts thereof.

Centers of chirality in the compounds of the formula I–IV may, unless indicated otherwise, be present in the R or S configuration. The invention relates both to the optically pure compounds and to mixtures of stereoisomers such as mixtures of enantiomers and mixtures of diastereomers.

Of the compounds according to the invention of the formula I–IV, all of which have a saccharide framework, the preferred compounds are those in which the configuration of the saccharide framework corresponds to that of 1-O-β-D-manno-pyranosyl-(2R,3S)-erythritol (formula V):

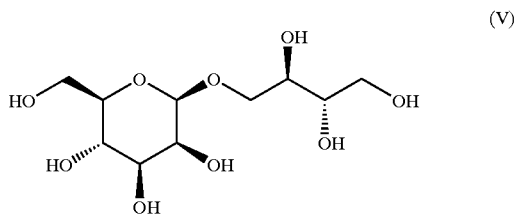

(V)

Some glycolipids with a mannopyranosyl-erythritol framework have already been mentioned in the literature (G. Deml et al. Phytochemistry, 19, 83–87, 1980). The schizonellins A and B described therein, which differ in their structure from the compounds according to the invention of the formula (I) to (IV), have weak antibiotic activity and a strong hemolytic effect.

The invention also relates to a method for the production of said compounds of the formula I to IV, which comprises cultivating the microorganism Ustilago maydis FH 2634 (DSM 11494) or mutants and variants thereof in an aqueous nutrient medium, and then isolating and purifying the target compounds.

The microorganism Ustilago maydis FH 2634 (DSM 11494) was isolated from a soil sample. Said microorganism was deposited on Apr. 14, 1997, under the conditions of the Budapest treaty at the Deutsche Sammlung von Mikroorganismen und Zelikulturen, Mascheroder Weg 1b, D-38124 Braunschweig under the number DSM 11494.

Ustilago maydis DSM 1494 has white aerial mycelium and gray spore chains. It forms characteristic spore chains. In a nutrient solution containing a source of carbon and a source of nitrogen and the usual inorganic salts, Ustilago maydis DSM 11494 produces ustilipides.

In place of the strain DSM 11494 it is also possible to employ its mutants and variants as long as they synthesize the compounds according to the invention. Such mutants can be generated in a manner known per se by physical means, for example irradiation, such as with ultraviolet rays or X-rays, or chemical mutagens such as, for example, ethyl-methanesulfonate (EMS); 2-hydroxy-4-methoxybenzophenone (MOB) or N-methyl-N'-nitro-N-nitrosoguanidine (MNNG). Screening for mutants and variants which produce the compounds according to the invention can take place by determining the biological activity of the active substances which have accumulated in the culture broth, for example by testing the dopamine-antagonistic effect by the method described below.

Suitable and preferred as source of carbon for the aerobic fermentation are assimilable carbohydrates and sugar alcohols such as glucose, lactose or D-mannitol, and carbohydrate-containing natural products such as, for example, malt extract. Suitable nitrogen-containing nutrients are: amino acids, peptides and proteins, and their degradation products such as peptones or tryptones, also meat extracts, ground seeds, for example of corn, wheat, beans, soybean or the cotton plant, distillation residues from the production of alcohol, meat meals or yeast extracts, but also ammonium salts and nitrates. Inorganic salts which the nutrient solution may contain are, for example, chlorides, carbonates, sulfates or phosphates of the alkali metals or alkaline earth metals, iron, zinc, cobalt and manganese.

The ustilipides are formed particularly well for example in a nutrient solution which contains about 0.5 to 5% glucose, preferably 1 to 2%, 0.5 to 5% soybean meal, preferably 1 to 2%, cornsteep, preferably 0.2 to 1%, 0.05 to 1.0% $CaCO_3$, preferably 0.1 to 0.5% and 0.1 to 2% NaCl, preferably 0.2 to 1%, in each case based on the weight of the complete nutrient solution.

The cultivation takes place aerobically, that is to say, for example, submerged with shaking or stirring in shaken flasks or fermenters, where appropriate with introduction of air or oxygen. The fermentation can be carried out, for example, in wide-necked bottles or round-bottomed flasks of various volumes, in glass fermenters or stainless steel tanks. It can be carried out in a temperature range of about 20 to 35° C., preferably at about 25 to 30° C. The pH should be between 3 and 10, advantageously between 4.5 and 8.5. The microorganism is cultivated under these conditions in general for a period of from 20 to 300 hours, preferably 24 to 140 hours. Cultivation is advantageously carried out in several stages, i.e. one or more precultures are initially produced in a liquid nutrient medium and are then transferred into the actual production medium, the main culture, for example in the ratio 1:10 by volume. The preculture is obtained, for example, by transferring a sporulated mycelium into a nutrient solution and allowing it to grow for about 20 to 120 hours, preferably 24 to 72 hours. The sporulated mycelium can be obtained, for example, by allowing the strain to grow for about 1 to 40 days, preferably 3 to 10 days, on a solid or liquid nutrient medium, for example yeast-malt agar or potato-dextrose agar.

The progress of the fermentation and the formation of the ustilipides can be followed according to methods known to the skilled worker, such as, for example, by testing the biological activity in bioassays or by chromatographic methods such as thin-layer chromatography (TLC) or high performance liquid chromatography (HPLC).

The ustilipides may occur both in the mycelium and in the culture filtrate, but the main amount is usually to be found in the biomass (mycelium). It is therefore expedient to separate the latter from the filtrate by filtration or centrifugation. The filtrate is extracted with a water-immiscible solvent such as, for example, 1-butanol, ethyl acetate, chloroform or the like. The mycelium is expediently extracted with methanol or acetone, but it is also possible to use the abovementioned water-immiscible solvents.

The extractions can be carried out in a wide pH range, but it is expedient to operate in a neutral medium, preferably between pH 4 and pH 8. The organic extracts can, for example, be concentrated in vacuo and dried.

One method for isolating the ustilipides is solution partition in a manner known per se.

Another method for purification is chromatography on adsorption resins such as, for example, on Diaion® HP-20 (Mitsubishi Casei Corp., Tokyo), on Amberlite® XAD 7 (Rohm and Haas, USA), on Amberchrom® CG, (Toso Haas, Philadelphia, USA) or the like. Also suitable are numerous reverse phase supports, for example $RP_{18}$, as have become generally known, for example, within the framework of high pressure liquid chromatography (HPLC).

Another possibility for purifying the compound according to the invention consists of the use of so-called normal phase chromatography supports such as, for example, silica gel or $Al_2O_3$ or others in a manner known per se. Suitable for this purpose are many solutions and mixtures thereof, such as, for example, chloroform/petroleum ether/alcohol mixtures to which acidic solvents such as, for example, acetic acid have been added.

An alternative isolation method is the use of molecular sieves such as, for example, Fractogel® TSK HW-40, Sephadex® LH-20 and others, in a manner known per se.

Besides the compounds of formula II, III and IV, the strain Ustilago maydis DSM 11494 also forms other very active compounds of the formula I which differ by the fatty acid composition and thus by the molecular formula and molecular weights from the compounds of the formula II, III and IV. Fatty acids from $C_2$ to $C_{20}$ can be detected, with saturated and unsaturated, branched and unbranched carboxylic acids such as, for example, stearic acid, linoleic acid, oleic acid or C-20 acid residues occurring. Thus, beside ustilipides A, B and C, the strain Ustilago maydis DSM 11494 also produces active glycoside esters with molecular weights of 648, 660, 674, 690, 700, 702, 704, 716, 718, 728, 730, 746 and 748. The glycoside framework of the ustilipides isolated from cultures of Ustilago maydis is the previously described 1-O-β-mannopyranosyl-(2R,3S)-erythritol (compound of the formula V).

The compounds of the formula I can be isolated and purified in analogy to the methods described above.

It has been found that the compounds according to the invention effectively antagonize dopamine D2 receptors, and, in particular, dopamine D3 receptors.

Dopamine (3,4-dihydroxyphenylethylamine) is a neurotransmitter which controls metabolic processes in the brain, and thus brain functions. Its effect takes place through docking on dopamine receptors. Various dopamine receptors which control different functions of the central nervous system have been described to date. Disturbance of the dopamine D3 receptor function has been recognized as an essential cause of schizophrenia (P. Sokoloff, J.-C. Schwartz et al. Nature, 347, 146–151, 1990). Hyperfunctioning thereof leads to pathological processes and therefore dopamine D3 antagonists are of great medical importance. However, dopamine receptor antagonists with a broad action reducing not only the pathological hyperfunctioning but also processes which are necessary for life are injurious: they cause unwanted side effects (D.S. Kreiss et al., Eur. J. Pharmacol. 277, 209–214, 1995). The compounds according to the invention, which selectively antagonize the D3 dopamine receptor, are particularly suitable for treating schizophrenia. The ustilipides according to the invention in some cases inhibit the dopamine D3 receptor considerably more strongly than the dopamine D2 receptor or other receptors and are therefore valuable novel agents for treating schizophrenia.

It has also been found, surprisingly, that the ustilipides according to the invention have only a slight hemolytic effect. In particular, the components which are fatty acid esters of higher carboxylic acids (C>10) show a negligible hemolytic effect up to concentrations of 100 mg per liter.

The present invention accordingly also relates to the use of the compounds according to the invention as pharmaceuticals, and to the use of the relevant compounds for the production of pharmaceuticals for the treatment and/or prophylaxis of schizophrenia, or for the treatment of disorders associated with a disturbance of the function of the dopamine D3 receptor.

Obvious chemical equivalents of the compounds according to the invention are compounds which show a slight chemical difference, that is to say have the same effect or are converted under mild conditions into the compounds according to the invention. Said equivalents include, for example, esters, amino derivatives, complexes or adducts of the or with the compounds according to the invention.

Physiologically tolerated salts of compounds of the formula 1,11, III or IV mean both the organic and the inorganic salts thereof as described in Remington's Pharmaceutical Sciences (17th edition, page 1418 (1985)). Because of the physical and chemical stability and the solubility, sodium, potassium, calcium and ammonium salts inter alia are preferred for acidic groups; salts of hydrochloric acid, sulfuric acid, phosphoric acid or of carboxylic acids or sulfonic acids, such as, for example, acetic acid, citric acid, benzoic acid, maleic acid, fumaric acid, tartaric acid and p-toluenesulfonic acid inter alia, are preferred for basic groups.

The present invention also relates to pharmaceuticals with a content of at least one compound according to the invention.

The pharmaceuticals according to the invention may be used enterally (orally), parenterally (intravenously), rectally or locally (topically). They can be administered in the form of solutions, powders, tablets, capsules (including microcapsules), liposome products, lipid complexes, colloidal dispersions or suppositories. Excipients suitable for such formulations are the pharmaceutically customary liquid or solid bulking agents and extenders, solvents, emulsifiers, lubricants, masking flavors, dyes, and/or buffer substances. It is expedient to administer a dosage of 0.1–100 mg/kg of bodyweight. They are expediently administered in dosage units which contain at least the effective daily amount of the compounds according to the invention, for example 30–3000 mg.

The invention further relates to pharmaceutical preparations which comprise one or more of the compounds according to the invention. The pharmaceuticals can be used, for example, in the form of pharmaceutical products which can be administered orally, for example in the form of tablets, coated tablets, hard or soft gelatine capsules, solutions, emulsions or suspensions. Inclusion of the pharmaceuticals in liposomes which, where appropriate, contain further components such as proteins is an administration form which is likewise suitable. They may also be administered rectally, for example in the form of suppositories, or parenterally, for example in the form of injection solutions. Pharmaceutical products can be produced by processing these compounds in therapeutically inert organic and inorganic carriers. Examples of such carriers for tablets, coated tablets and hard gelatine capsules are lactose, corn starch or derivatives thereof, talc and stearic acid or salts thereof. Carriers suitable for producing solutions are water, polyols, sucrose, invert sugar and glucose. Carriers suitable for injection solutions are water, alcohols, polyols, glycerol and vegetable oils. Carriers suitable for suppositories are vegetable oils and hardened oils, waxes, fats and semiliquid polyols. The pharmaceutical products may also contain preservatives, solvents, stabilizers, wetting agents, emulsifiers, sweeteners, dyes, flavorings, salts to alter the osmotic pressure, buffers, coating agents, antioxidants and, where appropriate, other therapeutic active substances.

The invention also relates to a method for the production of a pharmaceutical according to the invention, which comprises converting at least one of the compounds according to the invention with a pharmaceutically suitable and physiologically tolerated carrier and, where appropriate, further suitable active substances, additives or excipients into a suitable dosage form.

Preferred types of administration are oral and topical administrations, local administrations such as, for example, using a catheter or else injections.

The pharmaceutical products are preferably produced and administered in dosage units, each unit comprising as active ingredient a particular dose of the compound according to the invention or chemical derivatives derived therefrom. This dose can be in the case of solid dosage units such as tablets, capsules and suppositories up to about 200 mg, but preferably about 0.1 to 100 mg, and in the case of injection solutions in ampoule form up to about 200 mg, but preferably about 0.5 to 100 mg, per day.

The daily dose to be administered depends on the bodyweight, age, sex and condition of the mammal. However, higher or lower daily doses may also be appropriate in some circumstances. Administration of the daily dose can take place both by a single administration in the form of a single dosage unit or else in several smaller dosage units and by a multiple administration of divided doses at particular intervals.

The following examples are intended to explain the invention in more detail without wishing to restrict the scope of the invention in any way.

EXAMPLE 1

Production of a Spore Suspension of the Producer Strain Ustilago Maydis FH 2634, DSM 11494

100 ml of nutrient solution (20 g of malt extract, 2 g of yeast extract, 10 g of glucose, 0.5 g of $(NH_4)_2HPO_4$ in 1l of tap water, pH before sterilization, 6.0) in a 500 ml sterile Erlenmeyer flask are inoculated with the strain Ustilago maydis, FH 2634, DSM 11494, and incubated at 25° C. and 140 rpm on a rotary shaker for 72 hours. Then 120 ml of culture liquid are homogeneously dispersed in a sterile 500 ml Erlenmeyer flask containing the nutrient medium oatmeal infusion, 2.0 g/l, to which 15 g of agar/l have additionally been added for solidification, and decanted. The cultures are incubated at 25° C. for 10 to 14 days. The spores which have been produced after this time in the flask are rinsed out with 500 ml of deionized water which contains one drop of a commercially available nonionic surfactant (for example ®Triton X 100, from Serva) and immediately used further or stored at −22° C. in 50% glycerol or in 10% dimethyl sulfoxide at −140° C.

EXAMPLE 2

Production of a Culture or of a Preculture of the Producer Strain in an Erlenmeyer Flask A sterile 500 ml Erlenmeyer flask containing 100 ml of the nutrient solution described in Example 1 is inoculated with a culture which has grown in a slant tube or with 0.2 ml of pore suspension and incubated on a shaker at 140 rpm and 25° C. in the dark. The maximum production of the compounds of the formula I to IV is reached after about 72 hours. A 72-hour old submerged culture from the same nutrient solution is sufficient for inoculating 10 and 100 l fermenters (inoculum about 5%).

EXAMPLE 3

Production of the Ustilipides

A 10 l fermenter is operated under the following conditions:

| | |
|---|---|
| Nutrient medium: | Malt extract 20 g/l |
| | Yeast extract 2 g/l |
| | Glucose 10 g/l |
| | $(NH_4)_2HPO_4$ 2 g/l |
| | pH 6.0 (before sterilization) |
| Incubation time: | 48 or 72 hours, |
| Incubation temperature: | 25° C. |
| Stirrer speed: | 200 rpm, |
| Aeration: | 5 l of air/min. |

Foaming can be suppressed by a repeated addition of a few drops of ethanolic polyol solution. The production maximum is reached after 48 hours.

EXAMPLE 4

Isolation of the Ustilipide Complex 9l of the culture solution obtained in Example 3 are centrifuged, and the biomass (~1.3 l) is extracted by stirring twice with 3 L of methanol each time. The combined extracts are concentrated in vacuo and dried, and the dry matter (48 g) is dissolved with 25% isopropanol/75% water and loaded onto a column with a capacity of 3 l packed with adsorption resin MCI gel® CHP20P. Column dimensions: width×height: 11.3 cm×30 cm. Elution is with a solvent gradient from 25% isopropanol in water to 100% isopropanol and the outflow from the column is collected in fractions each of 2 l.

The ustilipide-containing fractions are collected and concentrated in vacuo, and freeze dried (8 g).

EXAMPLE 5

Concentration of the Ustilipide Components 5 g of the product obtained in Example 4 are loaded onto a column with a capacity of 3 liters packed with Fractogel® TSK HW-40 s (width×height=10 cm×50 cm). The mobile phase methanol is pumped at a flow rate of 50 ml per minute through the column, and the outflow from the column is collected in fractions (65 ml). The ustilipide complex (1.8 g) is found mainly in fractions 18 to 32. They are combined and freed of solvent in vacuo.

EXAMPLE 6

Separation of the Ustilipide Components 1.8 g of the ustilipide complex obtained in Example 5 are dissolved in chloroform and loaded onto a column with a capacity of 290 ml packed with silica gel. Elution takes place firstly with pure chloroform and then with chloroform mixtures with increasing methanol contents from 0 to 5% alcohol. Fractions of 50 ml are taken. The fractions are analyzed by dopamine D3/D2 inhibition tests and thin-layer chromatography using the α-naphthol/sulfuric acid reagent. The fractions containing mainly ustilipide A or B or C are each combined and concentrated in vacuo. This results in 105 mg of ustilipide A, 230 mg of ustilipide B and 170 mg of ustilipide C component in >50% purity.

EXAMPLE 7

Final Purification of the Ustilipide Components

The concentrated ustilipides A (104 mg), B (210 mg) and C (165 mg) obtained in Example 6 are each fractionated on a Nucleosil® 12$C_{18}$AB-HPLC column (width×height=3.2 cm×25 cm) in a gradient method with 50% to 80% acetonitrile in 0.05% trifluoroacetic acid. The fractions are investigated for purity by thin-layer chromatography and are combined appropriately, concentrated to vacuo and freeze dried. They afford 63 mg of ustilipide A in 96% purity, 162 mg of ustilipide B in 94% purity and 112 mg of ustilipide C in 95% purity.

The physicochemical and spectroscopic properties of the ustilipides can be summarized as follows:

Ustilipide A (Compound of the Formula II):

| | |
|---|---|
| Appearance: | Colorless oil which is soluble in alcohols and other organic solvents. Stable in neutral and weakly acidic medium but unstable in alkaline solution. |
| Molecular formula: | $C_{36}H_{64}O_{13}$ |
| Molecular weight: | 704 |
| $^1$H- and $^{13}$C-NMR: | see Table 1 |
| UV absorption: | End absorption. |
| $[\alpha]_D = -34°$ (c = 0.5 in chloroform) | |

Ustilipide B (Compound of the Formula lI):

| | |
|---|---|
| Appearance: | Colorless oil which is soluble in alcohols and other organic solvents. Stable in neutral and weakly acidic medium but unstable in alkaline solution. |
| Molecular formula: | $C_{34}H_{60}O_{13}$ |
| Molecular weight: | 676 |
| $^1$H- and $^{13}$C-NMR: | see Table 2 |
| UV absorption: | End absorption. |
| $[\alpha]_D = -33°$ (c = 0.5 in chloroform) | |

Ustilipide C (Compound of the Formula IV)

| | |
|---|---|
| Appearance: | Colorless oil which is soluble in alcohols and other organic solvents. Stable in neutral and weakly acidic medium but unstable in alkaline solution. |
| Molecular formula: | $C_{32}H_{58}O_{12}$ |
| Molecular weight: | 634 |
| $^1$H- and $^{13}$C-NMR: | see Table 3. |
| UV absorption: | End absorption. |
| $[\alpha]_D = -38°$ (c = 0.5 in chloroform) | |

TABLE 1

$^1$H- and $^{13}$C-NMR:
Chemical shifts of ustilipide A in $CDCl_3$ at 300K

| | $^1$H | $^{13}$C |
|---|---|---|
| 1 | 4.72 | 100.00 |
| 2 | 5.50 | 69.30 |
| 3 | 5.06 | 71.35 |
| 4 | 5.24 | 66.60 |
| 5 | 3.70 | 73.20 |
| 6 | 4.25/4.19 | 63.06 |
| 1α | 3.99/3.82 | 72.99 |
| 1β | 3.74 | 71.86 |
| 1γ | 3.65 | 72.55 |
| 1δ | 3.75 | 64.27 |
| 2C' | — | 174.16 |
| 2α | 2.43 | 34.80 |
| 2β | 1.65 | 25.37 |
| 2γ | 1.34 | 31.81 |
| 2δ | 1.34 | 22.97 |
| 2ε | 0.90 | 14.55 |
| 3C' | — | 173.42 |

TABLE 1-continued $^1$H- and $^{13}$C-NMR:
Chemical shifts of ustilipide A in CDCl$_3$ at 300K

|  | $^1$H | $^{13}$C |
|---|---|---|
| 3α | 2.21 | 34.70 |
| 3β | 1.53 | 25.39 |
| 3γ | 1.24 | 29.72 |
| 3δ-3ζ-3 | 1.36–1.21 | 30.35–29.90 |
| 3ζ-2 | 1.28 | 32.59 |
| 3ζ-1 | 1.28 | 23.35 |
| 3ζ | 0.87 | 14.78 |
| 4C' | — | 170.14 |
| 4-Me | 2.03 | 21.33 |
| 6C' | — | 171.46 |
| 6-Me | 2.09 | 21.39 |

TABLE 2

$^1$H- and $^{13}$C-NMR:
Chemical shifts of ustilipide B in CDCl$_3$ at 300K

|  | $^1$H | $^{13}$C |
|---|---|---|
| 1 | 4.73 | 99.97 |
| 2 | 5.50 | 69.33 |
| 3 | 5.06 | 71.38 |
| 4 | 5.24 | 66.58 |
| 5 | 3.70 | 73.13 |
| 6 | 4.25/4.18 | 63.04 |
| 1α | 3.99/3.79 | 72.92 |
| 1β | 3.73 | 71.83 |
| 1γ | 3.63 | 72.59 |
| 1δ | 3.71 | 64.21 |
| 2C' | — | 173.99 |
| 2α | 2.41 | 36.71 |
| 2β | 1.68 | 19.18 |
| 2γ | 0.98 | 14.20 |
| 2δ | — | — |
| 3C' | — | 173.41 |
| 3α | 2.20 | 34.68 |
| 3β | 1.52 | 25.35 |
| 3γ-3ζ-1 | 1.36–1.21 | 30.32–29.68 |
| 3ζ | 0.86 | 14.75 |
| 4C' | — | 170.15 |
| 4-Me | 2.02 | 21.31 |
| 6C' | — | 171.44 |
| 6-Me | 2.09 | 21.37 |

TABLE 3

$^1$H- and $^{13}$C-NMR:
Chemical shifts of ustilipide C in CDCl$_3$ at 300K

|  | $^1$H | $^{13}$C |
|---|---|---|
| 1 | 4.79 | 99.75 |
| 2 | 5.49 | 69.40 |
| 3 | 5.09 | 71.52 |
| 4 | 5.16 | 66.95 |
| 5 | 3.56 | 75.51 |
| 6 | 3.67 | 62.11 |
| 1α | 4.02/3.77 | 72.50 |
| 1β | 3.76 | 71.71 |
| 1γ | 3.64 | 72.86 |
| 1δ | 3.72 | 64.08 |
| 2C' | — | 177.56 |
| 2α | 2.68 | 34.63 |
| 2β | 1.21 | 19.96 |
| 2γ | 1.18 | 19.49 |
| 3C' | — | 173.41 |
| 3α | 2.20 | 34.69 |
| 3β | 1.52 | 25.37 |
| 3γ-3ζ-1 | 1.35–1.22 | 30.35–29.72 |
| 3ζ | 0.87 | 14.77 |
| 4C' | — | 170.76 |
| 4-Me | 2.04 | 21.37 |

EXAMPLE 8

Determination of the Biological Activity

The ustilipides effectively antagonize dopamine D2 and D3 receptors. One measure of their activity is the IC$_{50}$ which indicates the concentration of inhibitor at which the rate of the normal enzymatic reaction (or receptor antagonism) is reduced by 50%.

The inhibition constants determined for ustilipides A, B and C were as follows:

|  | Dopamine D3 IC$_{50}$: | Dopamine D2 IC$_{50}$: |
|---|---|---|
| Ustilipide A: | 5 µg/ml | 30 µg/ml |
| Ustilipide B: | 7 µg/ml | 16 µg/ml |
| Ustilipide C: | 12 µg/ml | 9 µg/ml |

Method for Determining the IC$_{50}$ Values:

The D$_3$ and D$_2$ long genes were isolated from a human cDNA library and stably transfected into CHO cells (CHO= Chinese hamster ovary). Membrane fractions are obtained from single clones with high-level expression. The binding assay is carried out in 96-well plates at room temperature for 60 minutes. The reaction mixture contains 50 µl of [N-methyl-$^3$H]spiroperidol, 50 µl of test substance or S(−)-eticlopride made for nonspecific binding and 100 µl of membrane. The assay is stopped by rapid filtration through a GF/B filter into a Skatron 96 cell harvester. The filters are cut up and placed in containers (T trays, Wallac), and the radioactivity is determined in a scintillation counter.

The specific binding is defined as the difference between the total binding and the binding in the presence of 10 µM S(−)-eticlopride. The total binding corresponds approximately to 10% of the counts of the ligands employed in total.

The inhibition of the binding by a test substance is calculated by correlation with the control reaction. Analysis of the data took place using the LIGAND software package of McPherson, Munson & Rodbard, Elsevier-BIOSOFT.

EXAMPLE 9

It is known of the schizonellins A and B, which have a structure similar to the compounds according to the invention, that they have a very strong hemolytic effect (G. Deml et al. Phytochemistry, 19, 83–87, 1980), which makes these compounds unsuitable for parenteral administration. On use of the schizonellins, a fatal 100% hemolysis occurs at concentrations as low as 10 and 30 µg/ml respectively. Determination of the hemolytic effect of ustilipides A, B and C gave the following results, the hemolysis being measured by the percentage of ruptured cells.

|  | Ustilipide C | Ustilipide B | Ustilipide A |
|---|---|---|---|
| 125 μg/ml | 0.8% | 0.4% | 0.1% |
| 62.5 μg/ml | 0.5% | 0.0% | 0.0% |
| 32 μg/ml | 0.4% | 0.0% | 0.0% |
| 16 μg/ml | 0.4% | 0.0% | 0.0% |
| 8 μg/ml | 0.0% | 0.0% | 0.0% |

The hemolysis experiments were carried out with human erythrocytes.

Determination of the In Vitro Hemolysis:

Venous blood freshly taken from humans, rhesus monkeys or beagle dogs is used to measure the hemolytic activity. The blood is collected in heparinized tubes and distributed in aliquots of 200 μl to 12 polyethylene tubes. One aliquot is mixed with 200 μl of distilled water and serves as 100% standard, and another is mixed with 200 μl of physiological saline (0.9% NaCl) (0% standard). 200 μl portions of substance dilutions in physiological saline to 1600, 800, 400, 200, 100, 50, 25, 12.5, 6.25 and 2.125 μl are distributed to the other tubes. All the tubes are cautiously agitated and then incubated at 37° C. for 3 hours. The 100% standard is then made up with 5 ml of distilled water, and the other tubes are each made up with 5 ml of physiological saline, and are centrifuged at 700 g for 5 minutes.

The hemolysis is determined by measuring the absorption of the supernatant in a spectrophotometer at a wavelength of 540 nm. The absorption of the standard with complete hemolysis is set at 100%. The absorption of the test product dilutions and of the 0% standard are measured and stated as a percentage of the maximum inducible hemolysis.

I. IDENTIFICATION OF THE MICROORGANISM

| Identification reference given by the DEPOSITOR: | Accession number issued by the INTERNATIONAL DEPOSITARY AUTHORITY: |
|---|---|
| FH 2634 | DSM 11494 |

II. SCIENTIFIC DESCRIPTION AND/OR PROPOSED TAXONOMIC DESIGNATION

The microorganism identified in section I was accompanied by:
☐ a scientific description
☒ a proposed taxonomic designation
(Indicate as applicable)

III. RECEIPT AND ACCEPTANCE

The present International Depositary Authority accepts the microorganism identified in section I, which it received on 01-04-1997 (date of the original deposit)[1]

IV. RECEIPT OF A REQUEST FOR CONVERSION

The present international Depositary Authority received the microorganism identified under section I on (date of the original deposit) and received a request for conversion of the original deposit conforming to the Budapest Treaty on (date of receipt of the request for conversion)

V. INTERNATIONAL DEPOSITARY AUTHORITY

| Name: | DSMZ-DEUTSCHE SAMMLUNG VON MIKROORGANISMEN UND ZELLKULTUREN GmbH | Signature(s) of the person(s) having the power to represent the International Depositary Authority, or of authorized official(s) |
|---|---|---|
| Address: | Mascheroder Weg 1b D-38124 Braunschweig | Date: V. Weiks 14-04-1997 |

[1]If Rule 6.4.d) applies, this date shall be the date on which the status of the international depositary authority was acquired.

| I. DEPOSITOR | II. IDENTIFICATION OF THE MICROORGANISM |
|---|---|
| Name: Hoechst Marion Roussel Core Research Functions | Accession number given by the INTERNATIONAL DEPOSITARY AUTHORITY: DSM 11494 |
| Address: H 780 | Date of the deposit or of the transfer[1]: |
| 65926 Frankfurt am Main | 01-04-1997 |

III. VIABILITY STATEMENT

The viability of the microorganism identified under section II above was tested on 01-04-1997[2]. On that date, the said microorganism was
☒[1] viable
☐[3] no longer viable -continued

IV. CONDITIONS UNDER WHICH THE VIABILITY TEST HAS BEEN PERFORMED[4]

V. INTERNATIONAL DEPOSITARY AUTHORITY

| Name: | DSMZ-DEUTSCHE SAMMLUNG VON MIKROORGANISMEN UND ZELLKULTUREN GmbH | Signature(s) of the person(s) having the power to represent the International Depositary Authority, or of authorized official(s) |
|---|---|---|
| Address: | Mascheroder Weg 1b D-38124 Braunschweig | Date: V. Weiks 14-04-1997 |

[1]Indicate the date of the original deposit or, where a new deposit or a transfer has been made, the most recent relevant date (date of the new deposit or date of the transfer).
[2]In the cases referred to in Rule 10.2(a)(ii) and (iii), refer to the most recent viability test.
[3]Mark with a cross the applicable box.
[4]Fill in if the information has been requested and if the results of the test were negative.

Patent claims:

1. A compound of the formula I

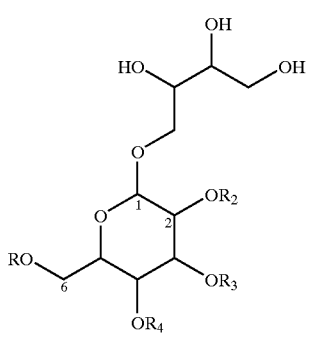

where $R_2$, $R_3$ and $R_4$ are, independently of one another, acyl radicals with 2–25 carbon atoms, which are unsubstituted or are substituted, independently of one another, by 1, 2 or 3 ($C_6$–$C_{12}$)-aryl radicals; and R is hydrogen or a radical defined under $R^2$, $R^3$ and $R^4$, where in the case where R is hydrogen, then $R^2$ is an acyl radical with 3–25 carbon atoms, which is unsubstituted or substituted by 1, 2 or 3 ($C_6$–$C_{12}$)-aryl radicals;

or a physiologically tolerated salt thereof.

2. A compound as claimed in claim 1, in which:

R is hydrogen or an acyl radical with 2–25 carbon atoms;
$R^2$ is an acyl radical with 4–25 carbon atoms;
$R^3$ is an acyl radical with 10–25 carbon atoms; and
$R^4$ is an acyl radical with 2–25 carbon atoms;
or a physiologically tolerated salt thereof.

3. A method for the production of a compound as claimed in claim 1, which comprises fermenting the microorganism Ustilago maydis DSM 11494 or one of its variants or mutants under suitable conditions to obtain ustilipides, isolating one or more of the ustilipides, and converting the latter where appropriate into physiologically tolerated salts.

4. The method as claimed in claim 3, wherein the fermentation is carried out under aerobic conditions at a temperature between 20 and 35° C. and at a pH between 3 and 10.

5. A method for antagonizing the dopamine D2 and/or dopamine D3 receptor, which comprises contacting the D2 and/or D3 receptor with a compound as claimed in claim 1.

6. A method for the treatment of schizophrenia or other disorder caused by dysfunction of dopamine metabolism, which comprises administering to a host in need of the treatment an effective amount of a compound as claimed in claim 1.

7. A pharmaceutical, which comprises an effective amount of at least one compound as claimed in claim 1, and a carrier.

8. A compound of the formula (II)

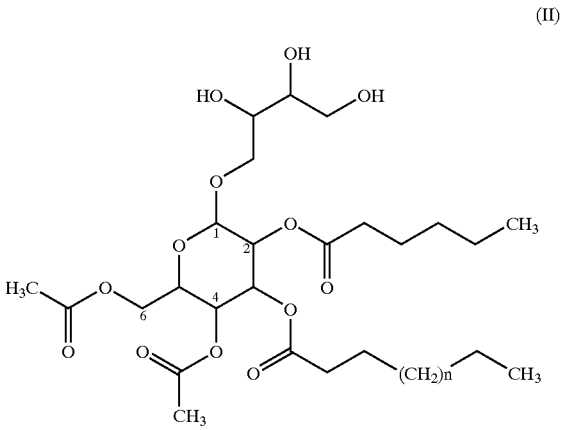

where n is 11;
or a physiologically tolerated salt thereof.

9. A method for the production of a compound as claimed in claim 8, which comprises fermenting the microorganism Ustilago maydis DSM 11494 or one of its variants or mutants under suitable conditions to obtain ustilipides, isolating one or more of the ustilipides, and converting the latter where appropriate into physiologically tolerated salts.

10. The method as claimed in claim 9, wherein the fermentation is carried out under aerobic conditions at a temperature ranging from 20 to 35° C. and at a pH between 3 and 10.

11. A method for antagonizing the dopamine D2 and/or dopamine D3 receptor, which comprises contacting the D2 and/or D3 receptor with a compound as claimed in claim 8.

12. A method for the treatment of schizophrenia or other disorder caused by dysfunction of dopamine metabolism, which comprises administering to a host in need of the treatment an effective amount of a compound as claimed in claim 8.

13. A pharmaceutical, which comprises an effective amount of at least one compound as claimed in claim 8, and a carrier.

14. A compound of the formula (III)

(III)

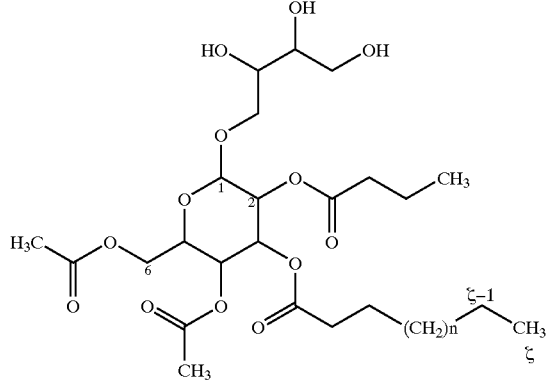

where n is 11;
or a physiologically tolerated salt thereof.

15. A method for the production of a compound as claimed in claim 14 which comprises fermenting the microorganism Ustilago maydis DSM 11494 or one of its variants or mutants under suitable conditions to obtain ustilipides, isolating one or more of the ustilipides, and converting the latter where appropriate into physiologically tolerated salts.

16. The method as claimed in claim 15, wherein the fermentation is carried out under aerobic conditions at a temperature ranging from 20 to 35° C. and at a pH between 3 and 10.

17. A method for antagonizing the dopamine D2 and/or dopamine D3 receptor, which comprises contacting the D2 and/or D3 receptor with a compound as claimed in claim 14.

18. A method for the treatment of schizophrenia or other disorder caused by dysfunction of dopamine metabolism, which comprises administering to a host in need of the treatment an effective amount of a compound as claimed in claim 14.

19. A pharmaceutical, which comprises an effective amount of at least one compound as claimed in claim 14, and a carrier.

20. A compound of the formula (IV)

(IV)

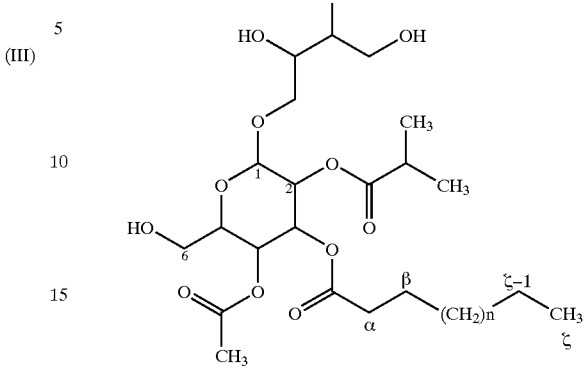

where n is 11;
or a physiologically tolerated salt thereof.

21. A method for the production of a compound as claimed in claim 20, which comprises fermenting the microorganism Ustilago maydis DSM 11494 or one of its variants or mutants under suitable conditions to obtain ustilipides, isolating one or more of the ustilipides, and converting the latter where appropriate into physiologically tolerated salts.

22. The method as claimed in claim 21, wherein the fermentation is carried out under aerobic conditions at a temperature ranging from 20 to 35° C. and at a pH between 3 and 10.

23. A method for antagonizing the dopamine D2 and/or dopamine D3 receptor, which comprises contacting the D2 and/or D3 receptor with a compound as claimed in claim 20.

24. A method for the treatment of schizophrenia or other disorder caused by dysfunction of dopamine metabolism, which comprises administering to a host in need of the treatment an effective amount of a compound as claimed in claim 20.

25. A pharmaceutical, which comprises an effective amount of at least one compound as claimed in claim 20, and a carrier.

26. The isolated microorganism Ustilago maydis DSM 11494.

* * * * *